United States Patent
Chen et al.

(10) Patent No.: US 9,372,095 B1
(45) Date of Patent: Jun. 21, 2016

(54) MOBILE ROBOTS MOVING ON A VISUAL DISPLAY

(71) Applicant: Google Inc., Mountain View, CA (US)

(72) Inventors: Charles L. Chen, San Jose, CA (US); Tiruvilwamalai Venkatram Raman, San Jose, CA (US)

(73) Assignee: Google Inc., Mountain View, CA (US)

( * ) Notice: Subject to any disclaimer, the term of this patent is extended or adjusted under 35 U.S.C. 154(b) by 90 days.

(21) Appl. No.: 14/273,107

(22) Filed: May 8, 2014

(51) Int. Cl.
| | | |
|---|---|---|
| *G01C 21/36* | (2006.01) | |
| *G06F 3/01* | (2006.01) | |
| *G06F 3/0354* | (2013.01) | |
| *G06F 3/038* | (2013.01) | |
| *G05D 1/02* | (2006.01) | |

(52) U.S. Cl.
CPC ........ *G01C 21/3652* (2013.01); *G01C 21/3629* (2013.01); *G05D 1/0231* (2013.01); *G06F 3/016* (2013.01); *G06F 3/0383* (2013.01); *G06F 3/03543* (2013.01); *G06F 3/03548* (2013.01)

(58) Field of Classification Search
CPC . G06F 3/016; G06F 3/03543; G06F 3/03548; G06F 3/0383; G05D 1/0231
USPC .......... 701/431, 523, 516, 519, 538; 345/584, 345/173, 175, 157; 340/407.2; 700/245, 700/248, 259, 264; 715/702
See application file for complete search history.

(56) References Cited

U.S. PATENT DOCUMENTS

| | | | | | |
|---|---|---|---|---|---|
| 5,625,576 | A * | 4/1997 | Massie | ................... | B25J 9/1689 318/628 |
| 5,643,087 | A * | 7/1997 | Marcus | ................... | A63F 13/06 273/148 B |
| 5,736,978 | A * | 4/1998 | Hasser | ................... | G06F 3/016 345/156 |
| 6,424,333 | B1 * | 7/2002 | Tremblay | ................ | G06F 3/011 345/156 |
| 6,532,140 | B1 | 3/2003 | McMahon et al. | | |
| 6,864,877 | B2 * | 3/2005 | Braun | ..................... | G06F 3/016 345/156 |
| 6,906,697 | B2 * | 6/2005 | Rosenberg | .......... | G06F 3/03543 345/156 |
| 7,084,854 | B1 * | 8/2006 | Moore | ................ | G06F 3/03543 345/156 |
| 8,441,444 | B2 * | 5/2013 | Moore | .................... | G06F 3/016 345/161 |
| 8,542,021 | B2 | 9/2013 | Scott et al. | | |
| 8,564,307 | B2 | 10/2013 | Kolker et al. | | |
| 8,723,820 | B1 * | 5/2014 | Han | ........................ | G03F 3/016 178/18.01 |
| 2002/0084982 | A1 * | 7/2002 | Rosenberg | .......... | G06F 3/03543 345/157 |
| 2005/0030284 | A1 * | 2/2005 | Braun | ..................... | G06F 3/016 345/156 |
| 2005/0052415 | A1 * | 3/2005 | Braun | ..................... | G06F 3/016 345/161 |
| 2006/0024647 | A1 * | 2/2006 | Chesnais | .............. | G09B 21/005 434/114 |
| 2006/0192760 | A1 * | 8/2006 | Moore | .................... | G06F 3/016 345/163 |
| 2007/0291035 | A1 * | 12/2007 | Vesely | .................... | G06F 3/011 345/427 |
| 2011/0155044 | A1 * | 6/2011 | Burch | ..................... | G06F 3/016 116/205 |
| 2012/0316698 | A1 | 12/2012 | Daniel | | |
| 2013/0307829 | A1 * | 11/2013 | Libin | ..................... | G06F 3/016 345/179 |

OTHER PUBLICATIONS

Eaton Corporation, "Cutler-Hammer, Warning," PUB-49439 REV (5) ECN-SOB-0270, Aug. 16, 2001, 1 page.
Powerlink AS, "Lighting Control System Catalog," Square D, Groupe Schneider, Sep. 1998, 49 pages.

* cited by examiner

*Primary Examiner* — Russell Frejd
(74) *Attorney, Agent, or Firm* — Fish & Richardson P.C.

(57) ABSTRACT

A system for using mobile robots that track visual features of a drawing to create a tangible tactile interface for a user. The user places a hand or finger on a mobile robot to trace and consequently cognize features of interest. The mobile robot tracks visual features and reports a location of the mobile robot to a guidance system. The guidance system presents location information to the user.

20 Claims, 7 Drawing Sheets

MOBILE ROBOTS MOVING ON A VISUAL DISPLAY

BACKGROUND

This specification relates to mobile robots moving on a visual display.

Line drawings are used to convey a wide variety of spatial information such as the layout of city streets and public transit lines. Producing tactile versions of such content (e.g., swell paper) for providing access to blind users is both expensive and time consuming. With the advent of touch screen devices, software applications can provide a level of access to such content via haptic feedback; however, haptic feedback on today's touchscreen devices can be far from realistic.

SUMMARY

This specification describes mobile robots that track visual features of a drawing to create a tangible tactile interface for a user. The user places a hand or finger on a mobile robot to trace and consequently cognize features of interest.

In general, one innovative aspect of the subject matter described in this specification can be embodied in a system comprising: a display surface displaying a plurality of visual features; a guidance system; and a mobile robot comprising: a drive system configured to drive the mobile robot over the display surface; a communication system configured to communicate with the guidance system; a sensor system configured to detect the visual features on the display surface; and a control system configured to cause the mobile robot to track, using the drive system and the sensor system, a first visual feature on the display surface, and to report, using the communication system, a location of the mobile robot to the guidance system while tracking the first visual feature; wherein the guidance system is configured to receive the location of the mobile robot and, in response, determine location information associated with the location of the mobile robot on the display surface and present the location information to a user in physical contact with a surface of the mobile robot.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. The display surface is an electronic display device, and wherein the guidance system is coupled to the electronic display device and configured to cause the electronic display device to display the visual features. The guidance system is a tablet computer and the electronic display device is a touchscreen. The first visual feature is a line, and wherein causing the mobile robot to track the first visual feature comprises executing a line following routine. The display surface displays a map, and wherein determining the location information associated with the location of the mobile robot on the display surface comprises accessing map data associating location information for geographic locations with corresponding locations on the map. Presenting the location information to the user comprises announcing the location information using an audio speaker. The display surface displays a map, and wherein determining the location information associated with the location of the mobile robot on the display surface comprises determining a street name marked on the map near the location of the mobile robot, and wherein announcing the location information comprises announcing the street name. The mobile robot comprises a haptic feedback system, and wherein presenting the location information to the user comprises sending an instruction to the mobile robot to actuate the haptic feedback system. The system includes a second mobile robot comprising a second drive system, a second communication system configured to communicate with the guidance system, a second sensor system, and a second control system; wherein the mobile robot comprises a first tactile feature and the second mobile robot comprises a second tactile feature different from the first tactile feature so that the user can distinguish the mobile robot and the second mobile robot by sense of touch. The display surface displays a map comprising first and second layers of information, and wherein the first visual feature represents a first element in the first layer of information, and wherein the second mobile robot is configured to track a second visual feature that represents a second element in the second layer of information.

Particular embodiments of the subject matter described in this specification can be implemented to realize one or more advantages. A system of mobile robots can create a tangible tactile interface to visual content such as line drawings, street maps, transit maps, and other forms of two-dimensional drawings that convey the spatial relationship amongst various entities. A user can experience the visual content by placing a hand or finger on a mobile robot as the mobile robot tracks visual features in the visual content. Different mobile robots can track different visual features that correspond to different layers of information in the visual content. A user can distinguish the mobile robots, and therefore the layers of information, by tactile features unique to each robot. A guidance system can present information associated with the visual display as the mobile robots track the visual features.

The details of one or more embodiments of the subject matter described in this specification are set forth in the accompanying drawings and the description below. Other features, aspects, and advantages of the subject matter will become apparent from the description, the drawings, and the claims.

BRIEF DESCRIPTIONS OF DRAWINGS

Like reference numbers and designations in the various drawings indicate like elements.

DETAILED DESCRIPTION

Figure 1A:
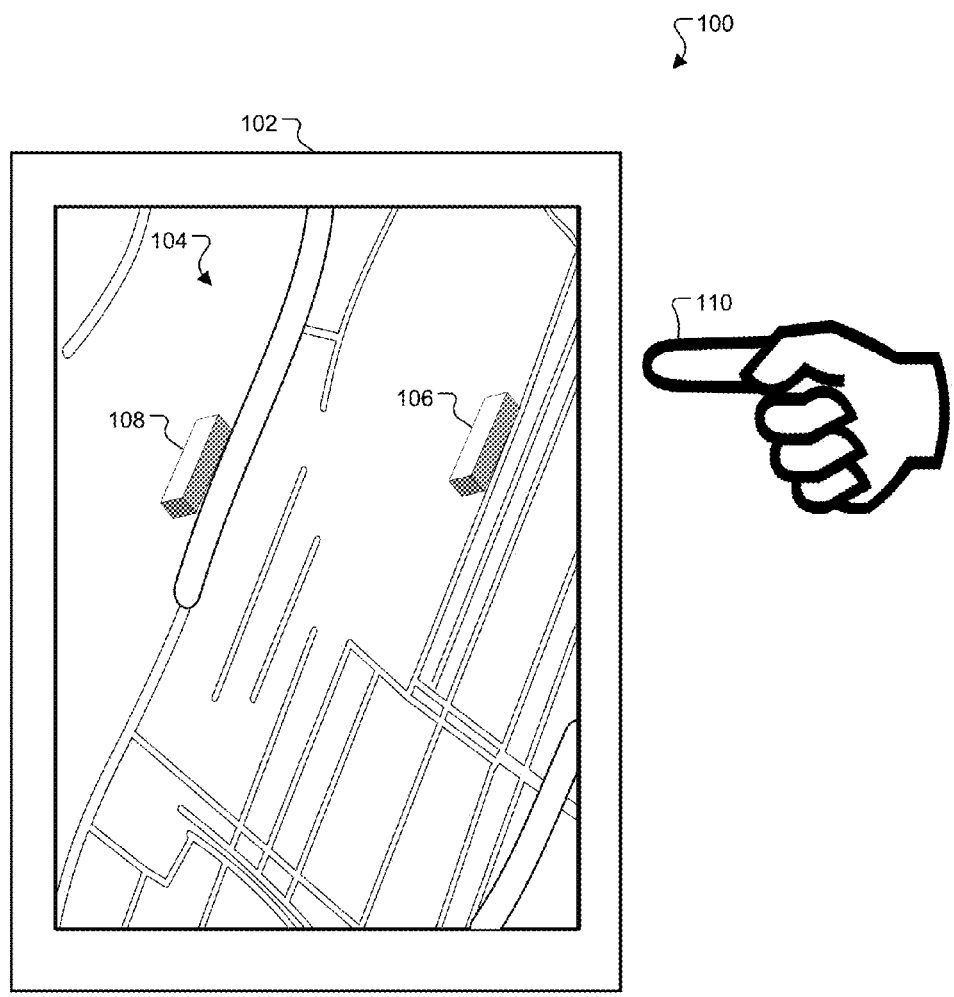
FIG. 1A is a diagram of an example system for experiencing visual content.

FIG. 1A is a diagram of an example system 100 for experiencing visual content. The system 100 includes a tablet computer 102 having a touchscreen 104 displaying a map. Two mobile robots 106 and 108 are tracking lines of different thicknesses on the map. A user places a hand or finger 110 onto one of the robots 106 as it tracks a line on the map.

While the robot 106 tracks the line, the robot wirelessly reports location information to the tablet computer 102. The tablet computer 102, in response, determines location information associated with the robot's location, e.g., a street name on the map. The tablet computer 102 presents the location information to the user, e.g., by announcing the street name using an audio speaker in the tablet computer.

The system 100 illustrated in FIG. 1A is just one example of a system for experiencing visual content using mobile robots.

Figure 1B:
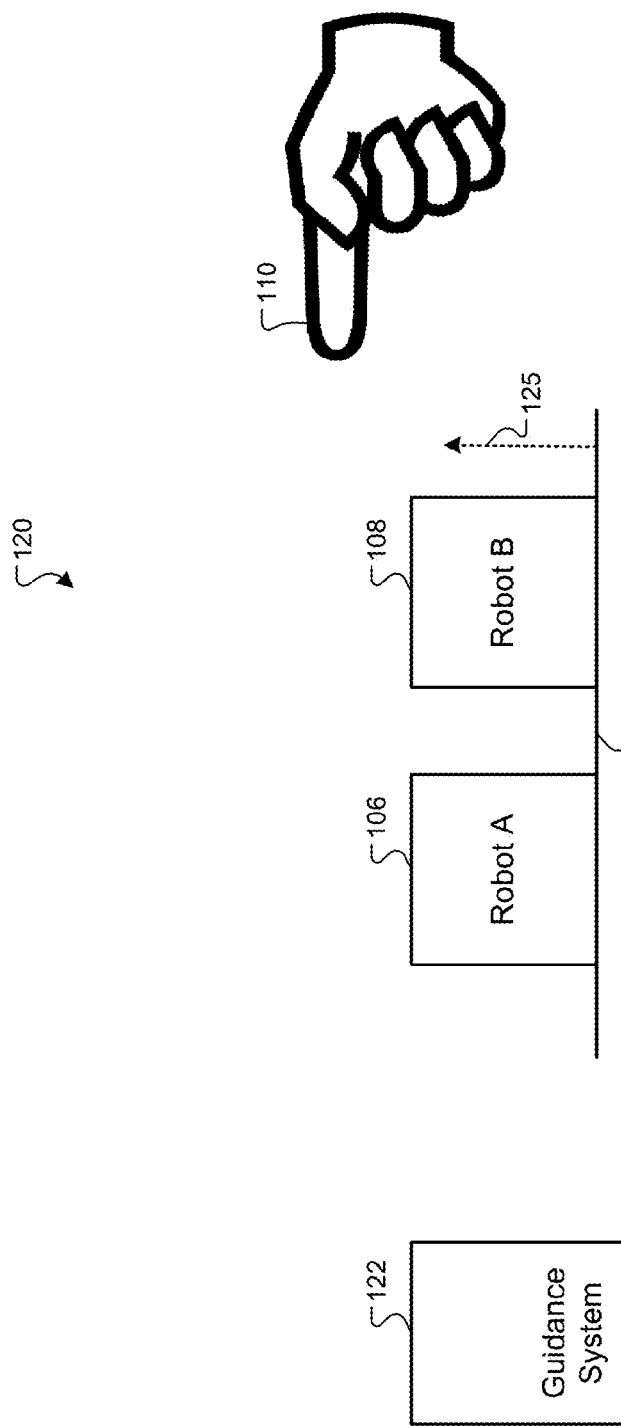
FIG. 1B is a block diagram of a general system for experiencing visual content using mobile robots.

FIG. 1B is a block diagram of a general system 120 for experiencing visual content using mobile robots. The system includes two robots 106 and 108 configured to move over a display surface 124. The display surface can be the touchscreen display 104 of FIG. 1A or any other appropriate type of display surface, e.g., an LCD screen oriented horizontally or even a piece of paper.

The display surface displays a number of visual features. For example, the display surface can display a map, which can have a variety of visual features, e.g., lines representing roads and transit lines. The map can display several layers of information. Lines having a certain thickness or color or other characteristic can represent one layer of information, e.g., street layouts, and lines having a different characteristic can represent a different layer of information, e.g., bus lines.

The robots 106 and 108 report location information to a guidance system 122. The guidance system 122 can be the tablet computer 102 of FIG. 1A or any other appropriate computing system, e.g., a personal computer or a server of one or more computers. The robots 106 and 108 communicate with the guidance system over a data communications network, e.g., via a Bluetooth link, or over WiFi.

The guidance system 122 executes software to receive the location information from the mobile robots and, in response, determine location information associated with the robots' locations. The guidance system 122 presents the location information to the user having a hand or finger 110 in contact with a surface of at least one of the robots.

The guidance system 122 is described further below with reference to FIGS. 4-5. One of the robots 106 is described further below with reference to FIGS. 2-3.

Figure 1C:
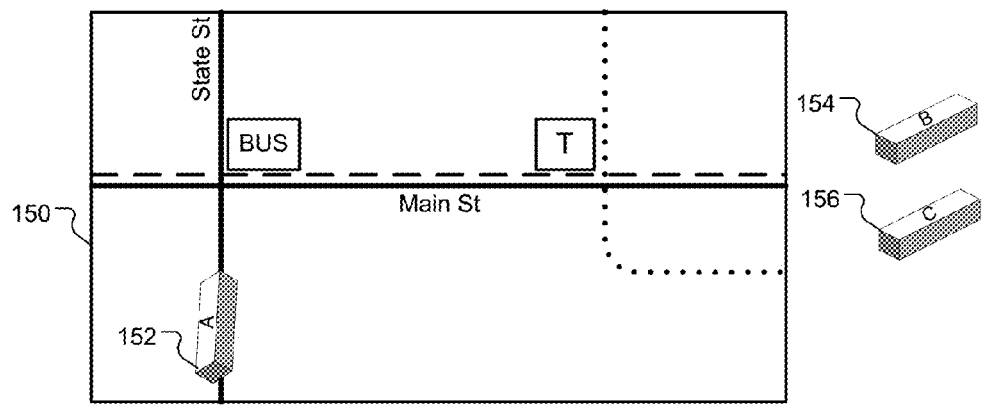
FIGS. 1C-1E illustrate an example scenario for using mobile robots to experience visual content.
Figure 1D:
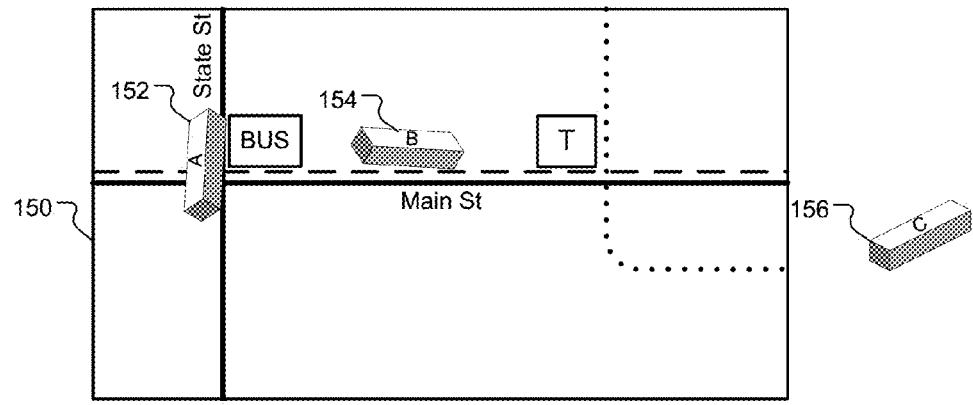
Figure 1E:
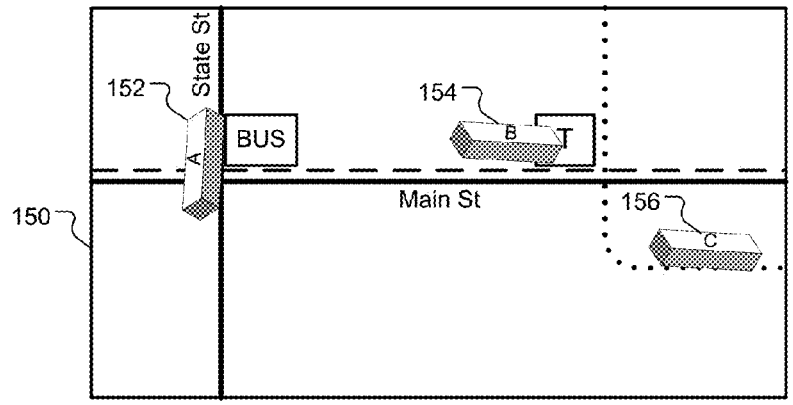

FIGS. 1C-1E illustrate an example scenario for using mobile robots to experience visual content. Such scenarios may facilitate the learning of routes, exploring different layers on a map, or even learning the interrelations of a complex system diagram.

FIG. 1C shows an example map 150 which is displayed on a display surface, e.g., the display surface 124 of FIG. 1B. A normal arrow 125 extends upward from the viewing plane of the display surface 124. The map contains three layers of information. One layer of information specifies streets on the map. Another layer of information specifies bus routes on the map. Another layer of information specifies train routes on the map.

The user has three robots 152, 154, and 156 available. The first robot 152 is configured to track solid lines that correspond to streets. The second robot 154 is configured to track dashed lines that correspond to bus routes. The third robot 156 is configured to track dotted lines that correspond to train routes.

The scenario begins with the user placing a first robot 152 on the display surface and activating the first robot 152. The first robot 152 begins tracking the a line corresponding to "State St." As the first robot 152 traces the route, the user can feel each turn on the route to build up a mental map of the route.

The first robot 152 sends its location to a guidance system, e.g., the guidance system 122 of FIG. 1B. The guidance system can announce to the user "you are now walking on State Street with an open-air shopping center on your right." When the robot approaches the intersection with Main St, the guidance system can announce to the user "you are now approaching an intersection with Main Street" and then "you are now approaching the Main Street bus stop."

The scenario continues as illustrated in FIG. 1D with the user parking the first robot 152 at the bus stop and placing the second robot 154 on the display surface, horizontal to the first robot 152. The user activates the second robot 154 and the second robot 154 begins tracking the line corresponding to the Main St bus route. The guidance system can announce "you are now riding on the Main Street bus route." As the second robot 154 approaches a train stop, the guidance system can announce "you are approaching the Main Street train stop."

The scenario continues as illustrated in FIG. 1E with the user parking the second robot 154 at the train stop and placing the third robot 156 on the display surface. The user activates the third robot 156 and the third robot begins tracking the line corresponding to the train route. The guidance system can announce "you are now riding on the Main Street train route."

The example scenario is presented for purposes of illustration and various other scenarios are possible. For example, the user can have multiple robots available to track lines corresponding to streets. The user can use the multiple robots to explore a neighborhood by tracking a main street with the first robot 152 and using other robots to explore side streets.

Furthermore, the features are not limited to maps or physical paths. For example, the robots can be used to explore a line-drawing illustrating the spatial relationship among components of a complex system. A multiplicity of autonomous robots as in the earlier use cases can be used to trace, explore and mark salient aspects of this system drawing to help a user build a mental model of the diagram and understand the information being conveyed.

Figure 2:
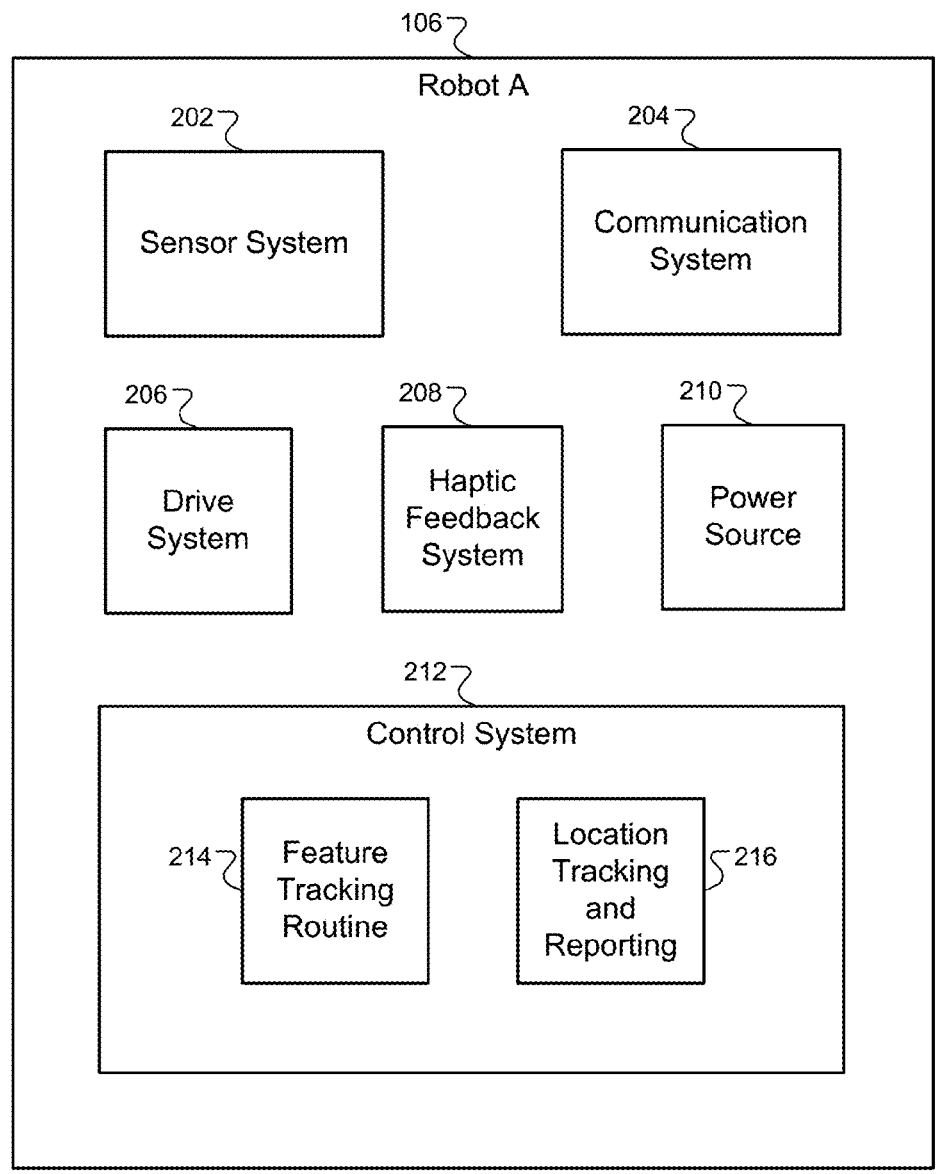
FIG. 2 is a block diagram of an example mobile robot for experiencing visual content.

FIG. 2 is a block diagram of an example mobile robot 106 for experiencing visual content. The robot 106 includes a sensor system 202 configured to detect visual features on a display surface. For example, the sensor system 202 can comprise a camera that faces the display surface, or a pair of light emitting diode (LED) emitter-detector circuits.

The robot 106 includes a communication system 204 configured to communicate with a guidance system over a data communications link. The communication system can be, e.g., a Bluetooth or Wi-Fi communication chip.

The robot 106 includes a drive system 206 configured to drive the robot 106 over the display surface. For example, the drive system 206 can include a pair of wheels or tracks and a pair of motors to drive the wheels or tracks. The robot 106 includes a haptic feedback system 208. The haptic feedback system 208 can be a simple vibration motor or a more complex device to provide various types of haptic feedback to a user that is in contact with the robot 106. The robot includes a power source 210. The power source 210 can be a battery or a solar cell or any other appropriate power source.

The robot 106 includes a control system 212. The control system 106 can be implemented as a microcontroller executing instructions stored on a computer readable medium. The control system 212 executes a feature tracking routine 214 and a location tracking and reporting routine 216.

The feature tracking routine 214 causes the mobile robot to track, using the drive system and the sensor system, a visual feature on the display surface. For example, the feature tracking routine 214 can be a line tracking routine. The line tracking routine can be configured to track a line of a certain thickness, a line blinking at a certain rate, a line following a certain pattern, or a line having a certain color.

The location tracking and reporting routine 216 causes the robot 106 to determine a location of the robot 106 on the display surface 124 and report the location to the guidance system 122. For example, the guidance system 122 can instruct the user to place the robot 106 in an initial position on the display surface 124, e.g., a far corner or edge of the surface having. The guidance system 122 then sends the initial location that was specified to the user to the control system 212 of the robot 106. The control system 212 then determines the robot's location, as it moves, based on how far the robot 106 has travelled from the initial location.

In some implementations, the mobile robots each include one or more unique tactile features so that the user can distinguish the mobile robots by sense of touch. For example, each robot can have a unique shape, or size, or texture.

Figure 3:
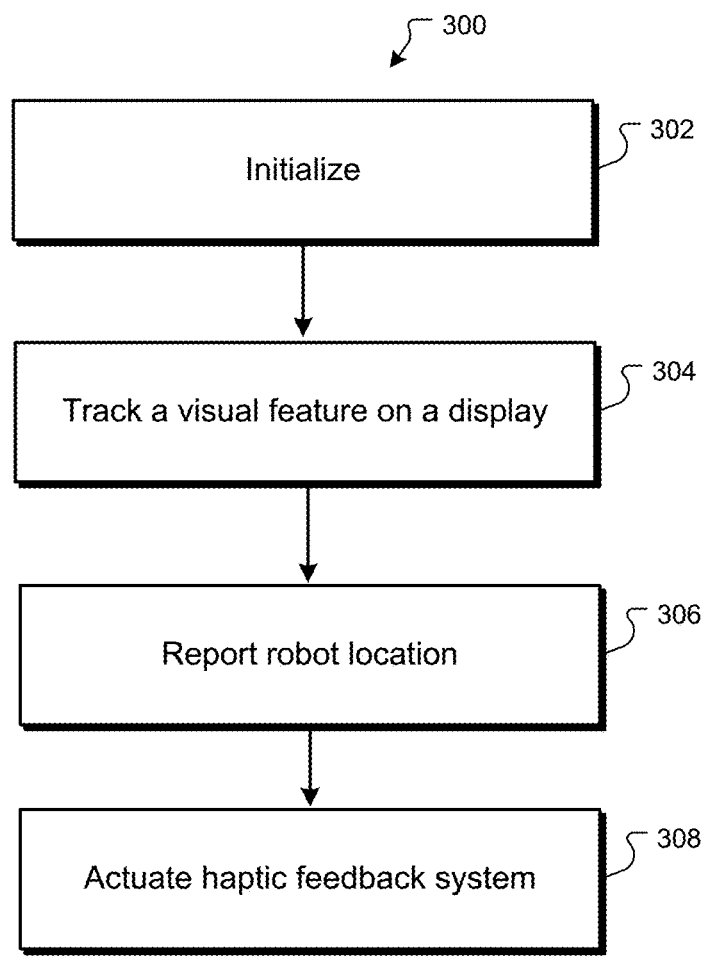
FIG. 3 is a flow diagram of an example process performed by the control system of the robot.

FIG. 3 is a flow diagram of an example process 300 performed by the control system 212 of the robot 106.

The control system 212 executes 302 an initialization routine in response to a user activating the robot 106, e.g., by flipping an "on" switch on the exterior of the robot 106. The initialization routine establishes a communications link with the guidance system, e.g., using a Bluetooth protocol, or by establishing a transmission control protocol (TCP) connection. The control system 212 also determines an initial location of the robot 106 while executing the initialization routine.

The control system 212 can determine the initial location using any of various appropriate techniques. In some implementations, the guidance system 122 sends the initial location, e.g., after instructing the user to place the robot 106 in a certain location. In some other implementations, the control system 212 uses the sensor system 202 to determine the initial location, e.g., by detecting certain features in an image captured by a camera.

The control system tracks 304 a visual feature on the display surface 124. For example, the control system 212 can execute a line following routine. The control system can track lines or other features having a specified thickness, color, or pattern. The user places a hand or finger on the robot 106 while the robot 106 is tracking the visual feature to build a mental map of the visual feature on the display surface 124.

The control system 212 determines the robot's location while it is tracking the visual feature and reports 306 the robot's location to the guidance system 122. For example, the control system 212 can report the robot's location periodically, after a certain period of time has passed or after the robot has travelled a certain distance. In some implementations, the control system 212 determines the robot's location based on the distance it has travelled from the initial position, e.g., using encoders installed in the drive system 206. In some other implementations, the control system 212 determines the robot's location by detecting known features on the display surface 124 using the sensor system 202.

The control system 212 can receive instructions from the guidance system 122 to actuate 308 the haptic feedback system. For example, the guidance system 122 can determine that the robot is at a location of interest and send an instruction the control system 212 to actuate the haptic feedback system to indicate to the user that the robot has reached the location of interest.

Figure 4:
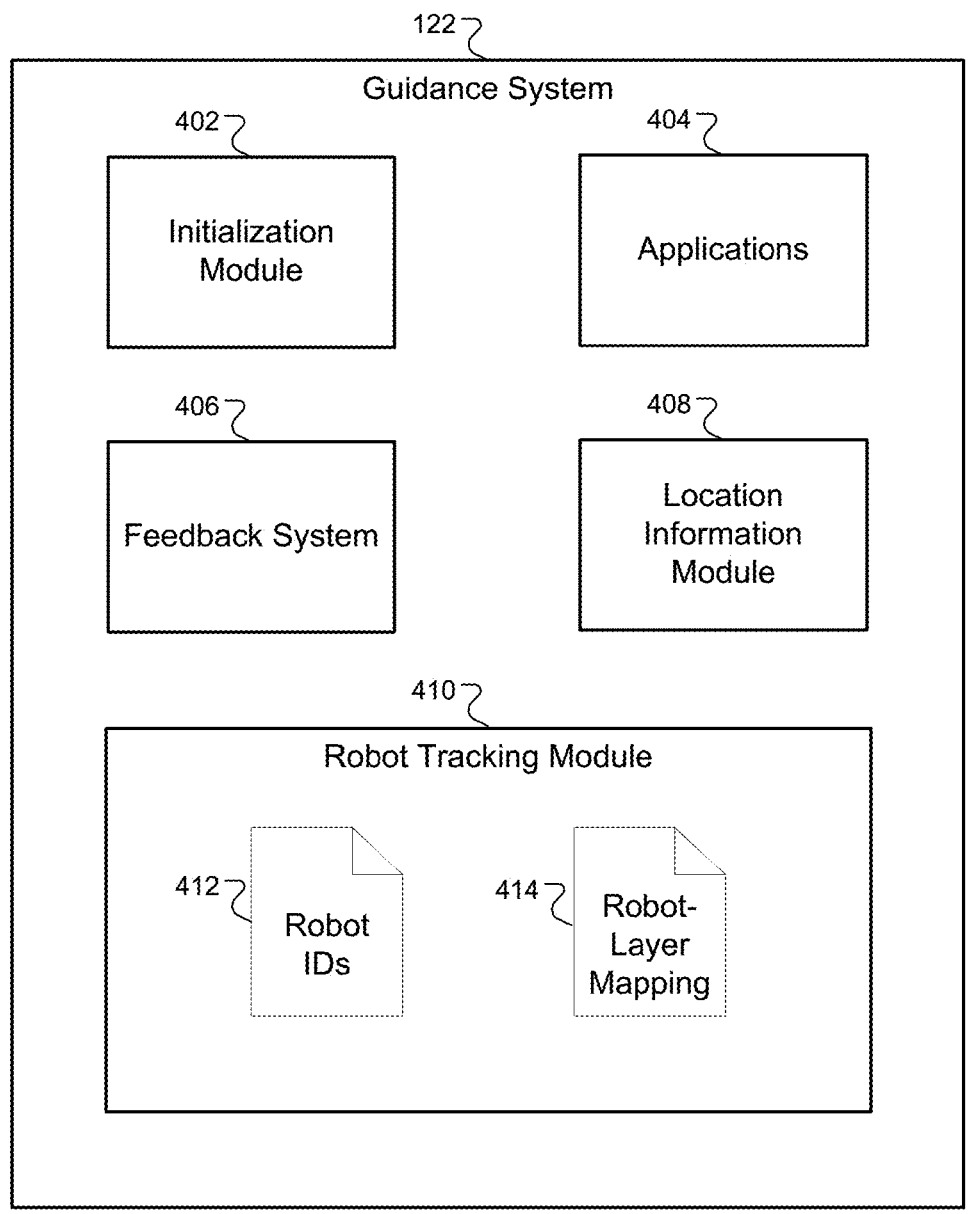
FIG. 4 is a block diagram of an example guidance system.

FIG. 4 is a block diagram of an example guidance system 122. The guidance system 122 is implemented as a system of one or more computers having software, firmware, hardware, or a combination of them that in operation cause the system to perform the guidance operations described below.

The guidance system 122 includes an initialization module 402. The initialization module 402 establishes a communications link with one or more mobile robots. In some implementations, the initialization module 402 sends an initial location to one or more mobile robots. For example, the guidance system 122 can announce to the user to place one of the mobile robots in a certain location and then send that mobile robot the initial location.

The guidance system 122 includes one or more applications 404. For example, one of the applications 404 can be a mapping application configured to display a map and provide directions between locations on the map. The mapping application can receive a starting location and an ending location from a user and then highlight a route on a map to display to the user. The mobile robots can track sections of the highlighted route to assist the user in building a mental map of the route.

The guidance system 122 includes a feedback system 406. The feedback system 406 can include an audio system of one or more speakers that the guidance system 122 uses to announce location information to the user. The feedback system 406 can include a haptic feedback system to provide haptic feedback to the user as the mobile robots travel over the display surface 124.

The guidance system 122 includes a location information module 408. The location information module is configured to receive a location of a mobile robot and, in response, determine location information associated with the location of the mobile robot on the display surface 124. The guidance system 122 can then present the location information to the user using the feedback system 406. For example, the location information module can translate the robot's location into a location on a map, which can then be provided to a mapping application. The mapping application can then supply location information, e.g., a street name to be announced.

The guidance system 122 includes a robot tracking module 410. The tracking module 410 stores a list of robot identifiers 412 to distinguish between one or more mobile robots that the user has placed on the display surface. Each mobile robot can have a unique identifier. The tracking module also stores a robot-layer mapping list 414 that specifies which robot corresponds to which layer of information on the display surface, e.g., which robot is configured to track streets and which robot is configured to track bus lines.

Figure 5:
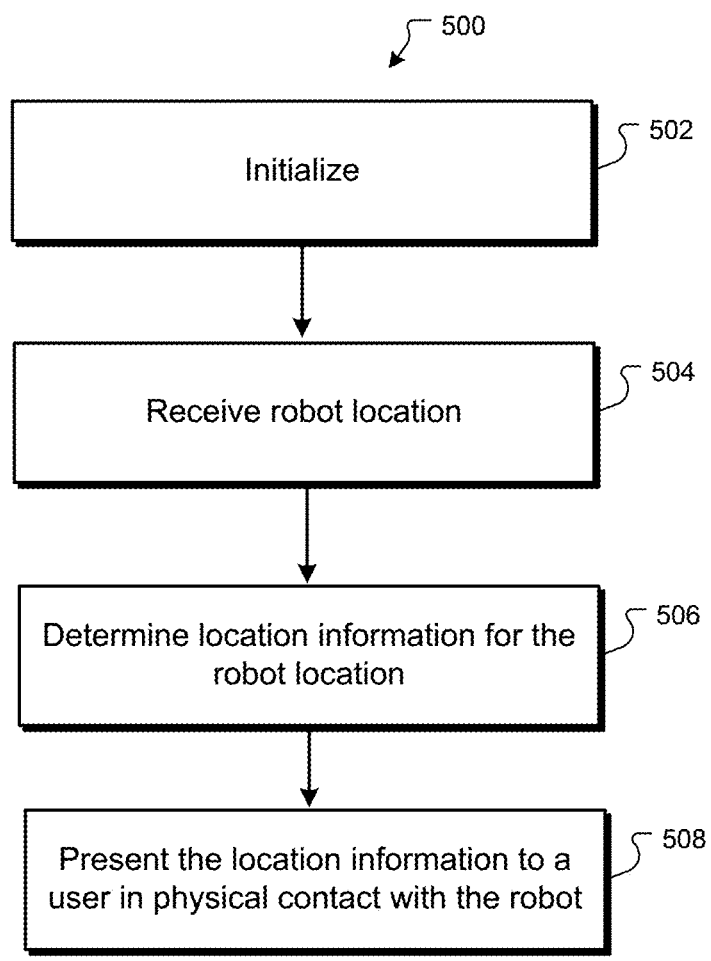
FIG. 5 is a flow diagram of an example process performed by the guidance system.

FIG. 5 is a flow diagram of an example process 500 performed by the guidance system 122.

The guidance system 122 executes 502 an initialization routine. For example, the guidance system 122 can cause the display surface to display a map, announce an instruction for the user to place a robot in one corner of the display surface, and then establish a communications link with robot. The guidance system 122 can send the robot an initial location.

The guidance system 122 receives 504 a location from the robot. The guidance system 122 determines 506 location information for the robot location. For example, the guidance system 122 map the location information for the robot location to x, y coordinates in the viewport. The x, y coordinates, in turn, are used to determine the name of a street that corresponds to a line that the robot is tracking on a map displayed on the display surface 124. The guidance system 122 presents 508 the location to the user who is in physical contact with the robot. For example, the guidance system 122 can announce the location information, or send an instruction to the robot for the robot to actuate a haptic feedback system.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, data processing apparatus. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry. The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. For example, the subject matter is described in context of scientific papers. The subject matter can apply to other indexed work that adds depth aspect to a search. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing can be advantageous.

What is claimed is:

1. A system comprising:
a display surface displaying a plurality of visual features;
a guidance system; and
a mobile robot comprising:
   a drive system configured to drive the mobile robot over the display surface, such that the mobile robot physically traverses across the display surface;
   a communication system configured to communicate with the guidance system;
   a sensor system configured to detect the visual features on the display surface; and
   a control system configured to cause the mobile robot to track, using the drive system and the sensor system, a first visual feature on the display surface, and to report, using the communication system, a location of the mobile robot to the guidance system while tracking the first visual feature;
wherein the guidance system is configured to receive the location of the mobile robot and, in response, determine location information associated with the location of the mobile robot on the display surface and present the location information to a user in physical contact with a surface of the mobile robot.

2. The system of claim 1, wherein the display surface is an electronic display device, and wherein the guidance system is coupled to the electronic display device and configured to cause the electronic display device to display the visual features.

3. The system of claim 2, wherein the guidance system is a tablet computer and the electronic display device is a touchscreen.

4. The system of claim 1, wherein the first visual feature is a line, and wherein causing the mobile robot to track the first visual feature comprises executing a line following routine.

5. The system of claim 1, wherein the display surface displays a map, and wherein determining the location information associated with the location of the mobile robot on the display surface comprises accessing map data associating location information for geographic locations with corresponding locations on the map.

6. The system of claim 1, wherein presenting the location information to the user comprises announcing the location information using an audio speaker.

7. The system of claim 6, wherein the display surface displays a map, and wherein determining the location information associated with the location of the mobile robot on the display surface comprises determining a street name marked on the map near the location of the mobile robot, and wherein announcing the location information comprises announcing the street name.

8. The system of claim 1, wherein the mobile robot comprises a haptic feedback system, and wherein presenting the location information to the user comprises sending an instruction to the mobile robot to actuate the haptic feedback system.

9. A system comprising:
a display surface displaying a plurality of visual features;
a guidance system; and
a mobile robot comprising:
   a drive system configured to drive the mobile robot over the display surface;
   a communication system configured to communicate with the guidance system;
   a sensor system configured to detect the visual features on the display surface;
   a control system configured to cause the mobile robot to track, using the drive system and the sensor system, a first visual feature on the display surface, and to report, using the communication system, a location of the mobile robot to the guidance system while tracking the first visual feature;
wherein the guidance system is configured to receive the location of the mobile robot and, in response, determine location information associated with the location of the mobile robot on the display surface and present the location information to a user in physical contact with a surface of the mobile robot, and
a second mobile robot comprising a second drive system, a second communication system configured to communicate with the guidance system, a second sensor system, and a second control system;
wherein the mobile robot comprises a first tactile feature and the second mobile robot comprises a second tactile feature different from the first tactile feature so that the user can distinguish the mobile robot and the second mobile robot by sense of touch.

10. The system of claim 9, wherein the display surface displays a map comprising first and second layers of information, and wherein the first visual feature represents a first element in the first layer of information, and wherein the second mobile robot is configured to track a second visual feature that represents a second element in the second layer of information.

11. A method performed by a guidance system comprising one or more computers configured to perform operations comprising:
receiving a location from a mobile robot tracking a visual feature displayed on a display surface, the tracking including the mobile robot physically traversing along the visual feature and across the display surface of an electronic device;
determining location information associated with the location of the mobile robot on the display surface; and
presenting the location information to a user in physical contact with a surface of the mobile robot.

12. The method of claim 11, comprising:
instructing the user to place the robot in a known location on the display surface; and
sending an initial location corresponding to the known location to the mobile robot.

13. The method of claim 11, wherein the display surface displays a map, and wherein determining the location information associated with the location of the mobile robot on the display surface comprises accessing map data associating location information for geographic locations with corresponding locations on the map.

14. The method of claim 11, wherein presenting the location information to the user comprises announcing the location information using an audio speaker.

15. The method of claim 14, wherein the display surface displays a map, and wherein determining the location information associated with the location of the mobile robot on the display surface comprises determining a street name marked on the map near the location of the mobile robot, and wherein announcing the location information comprises announcing the street name.

16. The method of claim 11, wherein presenting the location information to the user comprises sending an instruction to the mobile robot to actuate a haptic feedback system.

17. The method of claim 11, wherein the display surface is an electronic display device, and wherein the guidance system is coupled to the electronic display device and configured to cause the electronic display device to display the visual features.

18. The method of claim 17, wherein the guidance system is a tablet computer and the electronic display device is a touchscreen.

19. A method performed by a guidance system comprising one or more computers configured to perform operations comprising:
   receiving a location from a mobile robot tracking a visual feature on a display surface;
   determining location information associated with the location of the mobile robot on the display surface;
   presenting the location information to a user in physical contact with a surface of the mobile robot; and
   storing a list of robot identifiers for a plurality of robots on the display surface.

20. The method of claim 19, comprising storing a robot-layer mapping list that specifies which robot corresponds to which layer of a plurality of layers of information displayed on the display surface.

* * * * *